United States Patent
Minami et al.

(10) Patent No.: US 6,890,543 B2
(45) Date of Patent: May 10, 2005

(54) COMPOSITION FOR LIPSTICK

(75) Inventors: Takashi Minami, Yokohama (JP);
Kinya Hosokawa, Yokohama (JP);
Sumire Suzuki, Yokohama (JP);
Takayuki Miyazaki, Yokohama (JP);
Yoshikazu Soyama, Yokohama (JP);
Kunihiko Yoshida, Yokohama (JP);
Tomiyuki Nanba, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 09/890,190
(22) PCT Filed: Dec. 1, 2000
(86) PCT No.: PCT/JP00/08496
§ 371 (c)(1),
(2), (4) Date: Jul. 30, 2001
(87) PCT Pub. No.: WO01/39733
PCT Pub. Date: Jun. 7, 2001

(65) Prior Publication Data
US 2003/0035781 A1 Feb. 20, 2003

(30) Foreign Application Priority Data
Dec. 2, 1999 (JP) .......................................... 11-343962

(51) Int. Cl.⁷ ............................. A61K 6/00; A61K 7/00; A61K 7/025
(52) U.S. Cl. ......................................... 424/401; 424/64
(58) Field of Search ............................. 424/64, 401, 63

(56) References Cited

U.S. PATENT DOCUMENTS 5,672,339 A * 9/1997 Soyama et al. ............... 424/63

FOREIGN PATENT DOCUMENTS

| CN | 11115363 | | 11/1995 |
| EP | 0748622 A | | 12/1996 |
| EP | 0775496 A | | 5/1997 |
| JP | 59148713 A | * | 8/1984 |
| JP | 59-148713 A | * | 8/1984 |
| JP | 07-196437 | | 8/1995 |
| JP | 10-152412 | | 6/1998 |
| JP | 10-152414 | | 6/1998 |
| JP | 11-147809 | | 6/1999 |

* cited by examiner

Primary Examiner—Thurman K. Page
Assistant Examiner—S. Howard
(74) Attorney, Agent, or Firm—Townsend & Banta

(57) ABSTRACT

The present invention provides a lipstick composition which drastically improves the color development and also is superior in terms of spreadability, gloss, and long-lastingness The present invention also provides a lipstick composition with superior a shape-retaining ability without using ceresin for the shape-retaining agent. The present invention is a lipstick composition comprising (a) 3–25 mass % of one, two or more types of polyethylene wax (average molecular weight 300–700) and (b) 0.1–50 mass % of one, two or more types of liquid oil having one —OH group in the structure.

4 Claims, No Drawings

COMPOSITION FOR LIPSTICK

TECHNICAL FIELD

The present invention relates to a lipstick composition. More particularly, the present invention relates to a lipstick composition with superior spreadability, gloss, and long-lastingness. In addition, the present invention relates to a lipstick composition with a superior shape-retaining ability.

BACKGROUND ART

A lipstick is applied to the lips to put a color and gloss to the lips to draw charm; it is recognized as one of the makeup cosmetics with the highest cosmetic effect. "Color development" is one of the functions desired from a lipstick. Generally, wax, various liquid oils, powder which contains a colorant, and perfume are blended into a lipstick composition used for a lipstick; the combination helps maintain the spreadability, gloss, color development, long-lastingness, etc. which constitute the basic usability of a lipstick in relation to the aforementioned functions related to the quality.

The object of the present invention is to provide a lipstick composition which drastically improves the color development related to the basic usability of a lipstick and also is superior in terms of spreadability, gloss, and long-lastingness.

Also, the object of the present invention is to provide a lipstick composition with a superior shape-retaining ability, essentially without using ceresin which conventionally is used as a shape-retaining agent.

DISCLOSURE OF INVENTION

The inventors conducted earnest research to solve the aforementioned problem and discovered that a lipstick composition which drastically improves the color development and also is superior in terms of spreadability, gloss, and long-lastingness can be obtained by using polyethylene with a specific molecular weight for the wax ingredient and combining this with a specific liquid oil ingredient in a specific quantity ratio, thus completing the present invention.

In other words the present invention relates to a lipstick composition comprising (a) 3–25 mass % of one, two or more types of polyethylene wax (average molecular weight 300–700) and (b) 0.1–50 mass % of one, two or more types of liquid oil having one —OH group in the structure.

In the present invention, a lipstick composition refers to a broad range of compositions used for a lipstick which is a makeup cosmetic; it can take any form such as a stick, pencil, ointment, or liquid. The present invention can be applied to a lip cream which does not particularly contain a colorant for the sake of an improvement in usability in terms of spreadability and gloss.

BEST MODE FOR CARRYING OUT THE INVENTION

The present invention is described in detail below.

In the present invention, ingredient (a) is polyethylene wax with an average molecular weight of 300–700, preferably 500–700. Polyethylene wax is conventionally known as a solidifier, shape-retaining agent, etc. for oil-based cosmetics. In the present invention, if the average molecular weight of the polyethylene wax is less than 300 then the solidifying ability is reduced, which is not preferable; on the other hand, if it is more than 700 then the melting point becomes high and dissolution in the liquid oil ingredient becomes harder, which is not preferable either.

For ingredient (a), one, two or more types can be used. The blend ratio of ingredient (a) is 3–25 mass %, preferably 5–20 mass %, of the total amount of the composition. If the blend ratio is less than 3 mass % then the dispersibility of the pigment does not improve enough; on the other hand, if it is more than 25 mass % then spreadability at the time of application becomes poor, which is not preferable.

For ingredient (b) of the present invention, a liquid oil ingredient having one —OH group in its structure is used. Here, "a liquid oil ingredient" refers to an oil ingredient which is in a liquid form at ordinary temperatures. Specific examples of ingredient (b) include ester oils such as glyceryl diisostearate, diglyceryl triisostearate, and diisostearyl malate; of these, glyceryl diisostearate, diglyceryl triisostearate, and isostearyl oxystearate are preferable. For ingredient (b), one, two or more types can be used.

The blend ratio of ingredient (b) is 0.1–50 mass %, preferably 0.1–45 mass %, of the total amount of the composition. If the blend ratio is less than 0.1 mass % then the color development does not improve sufficiently; on the other hand, if it is more than 50 mass %, then spreadability at the time of application becomes poor, which is not preferable.

By combining ingredient (a) and ingredient (b) as described above, a lipstick composition with markedly improved color development of lips as well as superior spreadability, gloss, and long-lastingness can be obtained.

In addition to the aforementioned essential ingredients, any other ingredients which are commonly blended in a lipstick composition can be blended in; examples include shape-retaining agent, oil ingredients, and powder.

For the shape-retaining agent, wax such as carnauba wax, paraffin wax, and microcrystalline wax can be used in addition to polyethylene wax as the aforementioned ingredient (a); any one, two, or more can be selected from these. The total blend ratio in the composition of the present invention is preferably 3–25 mass %.

It is particularly preferable in terms of shape-retaining ability to blend the polyethylene wax of (a) and microcrystalline wax (c) in the ratio of 6:4–9:1. The blend ratio of the microcrystalline wax is normally 0.1–10 mass % in the composition.

For the oil ingredient, in addition to liquid oil that is the aforementioned ingredient (b), the following, for example, can be blended in: hydrocarbon oils such as squalane, liquid petrolatum, and petrolatum; higher fatty acids such as myristic acid, palimitic acid, stearic acid, 12-hydroxystearic acid, and behenic acid; higher alcohols such as cetyl alcohol, stearyl alcohol, oleyl alcohol, and batyl alcohol; esters such as cetyl-2-ethyl hexanoate, 2-ethylhexyl palmitate, 2-octyl dodecyl myristate, neopentyl glycol-2-ethyl hexanoate, glyceride trioctanoate, pentaerythritol trioctanoate, isopropyl myristate, myristyl myristate, and glyceride trioleate; fats and oils such as olive oil, avocado oil, jojoba oil, sunflower oil, safflower oil, tsubaki oil, shea butter, macademia nut oil, mink oil, lanolin, liquid lanolin, acetic acid lanolin, and castor oil; silicone oils such as dimethylpolysiloxane, methylphenyl poly siloxane, gum-like dimethylpolysiloxane with a high degree of polymerization, polyether degeneration silicone, amino-modified silicone, and gum-like amino-modified silicone with a high degree of polymerization; and fluorine oils such as perfluoro polyether and perfluoro carbon. In the present invention, the blend ratio of the oil is 50 mass % or more, preferably 70 mass % or more, of the total amount of the composition.

Examples of the powder include inorganic powders such as talc, kaolin, sericite, muscovite, phlogopite, synthetic mica, aluminum silicate, silica, barium sulfate, and calcium phosphate and organic powders such as nylon powder and cellulose powder, as well as various pigments. The blend ratio of powder is preferably 1–30 mass %, more preferably 0.1–15 mass % of the total amount of the composition.

In addition, antioxidants, ultraviolet absorbents, ultraviolet masking agents, preservatives, humectants, dyes, etc. can be blended in.

EXAMPLES

The present invention is described in detail below based on Examples; however, the present invention is not limited to these Examples. The blend ratio is shown as a mass % value of the total amount of the composition unless specified otherwise.

In Examples, the lipstick composition was evaluated with the following criteria for color development, spreadability, gloss, and long-lastingness.

[Color Development]
Each member of a panel of 15 specialists conducted the following five step evaluation, based on which the color development was evaluated.
(Rating)
1: Color development is poor.
2: Color development is somewhat poor.
3: Color development is normal.
4: Color development is somewhat good.
5: Color development is good.
(Evaluation of the color development)
⊚: The average rating is 4.5 or more and 5.0 or less.
○: The average rating is 3.5 or more and less than 4.5.
Δ: The average rating is 2.5 or more and less than 3.5.
X: The average rating is 1.5 or more and less than 2.5.
XX : The average rating is 1.0 or more and less than 1.5.

[Spreadability]
Each member of a panel of 15 specialists conducted the following five step evaluation, based on which the spreadability was evaluated.
(Rating)
1: Spreadability is poor.
2: Spreadability is somewhat poor.
3: Spreadability is normal.
4: Spreadability is somewhat good.
5: Spreadability is good.
(Evaluation of the Spreadability)
⊚: The average rating is 4.5 or more and 5.0 or less.
○: The average rating is 3.5 or more and less than 4.5.
Δ: The average rating is 2.5 or more and less than 3.5.
X: The average rating is 1.5 or more and less than 2.5.
XX: The average rating is 1.0 or more and less than 1.5.

[Gloss]
Each member of a panel of 15 specialistss conducted the following five step evaluation, based on which the gloss was evaluated.
(Rating)
1: Gloss is poor.
2: Gloss is somewhat poor.
3: Gloss is normal.
4: Gloss is somewhat good.
5: Gloss is good.
(Evaluation of the Gloss)
⊚: The average rating is 4.5 or more and 5.0 or less.
○: The average rating is 3.5 or more and less than 4.5.
Δ: The average rating is 2.5 or more and less than 3.5.
X: The average rating is 1.5 or more and less than 2.5.
XX: The average rating is 1.0 or more and less than 1.5.

[Long-Lastingness]
Each member of a panel of 15 specialists conducted the following five step evaluation, based on which the long-lastingness was evaluated.
(Rating)
1: Long-lastingness is poor.
2: Long-lastingness is somewhat poor.
3: Long-lastingness is normal.
4: Long-lastingness is somewhat good.
5: Long-lastingness is good.
(Evaluation of the Long-Lastingness)
⊚: The average rating is 4.5 or more and 5.0 or less.
○: The average rating is 3.5 or more and less than 4.5.
Δ: The average rating is 2.5 or more and less than 3.5.
X: The average rating is 1.5 or more and less than 2.5.
XX: The average rating is 1.0 or more and less than 1.5.

[The Shape-Retaining Ability]
The shape-retaining ability was evaluated based on the defect ratio (shrinkage pin-holes and surface peeling) after filling and molding.
(Evaluation of the Shape-Retaining Ability)
⊚: Defect ratio 0% or more and less than 1%
○: Defect ratio 1% or more and less than 5%
Δ: Defect ratio 5% or more and less than 10%
X: Defect ratio 10% or more Examples 1–6, Comparative Examples 1–7: Stick-Shaped Lipstick Compositions Lipstick compositions with composition blend ratios as shown in the following Table 1 were prepared, and color development, spreadability, gloss, and long-lastingness were evaluated for Examples and Comparative examples according to the aforementioned evaluation criteria. The results are shown in Table 1.

TABLE 1

| | Comparative Example | | Example | | | Comparative example | | | Example | | | Comparative Example | |
|---|---|---|---|---|---|---|---|---|---|---|---|---|---|
| | 1 | 2 | 1 | 2 | 3 | 3 | 4 | 5 | 4 | 5 | 6 | 6 | 7 |
| Ceresin | 15 | | | | | | 15 | | | | | | |
| Polyethylene wax (average molecular weight 250) | | 15 | | | | | | 15 | | | | | |
| Polyethylene wax (average molecular weight 300) | | | 15 | | | | | | 15 | | | | |
| Polyethylene wax (average molecular weight 500) | | | | 15 | | | | | | 15 | | | 15 |

TABLE 1-continued

|  | Comparative Example | | Example | | | Comparative example | | | Example | | | Comparative Example | |
|---|---|---|---|---|---|---|---|---|---|---|---|---|---|
|  | 1 | 2 | 1 | 2 | 3 | 3 | 4 | 5 | 4 | 5 | 6 | 6 | 7 |
| Polyethylene wax (average molecular weight 700) |  |  |  | 15 |  |  |  |  |  | 15 |  |  |  |
| Polyethylene wax (average molecular weight 800) |  |  |  |  | 15 |  |  |  |  |  | 15 |  |  |
| Glyceryl diisostearate | 20 | 20 | 20 | 20 | 20 | 20 |  |  |  |  |  |  |  |
| Diglyceryl triisostearate |  |  |  |  |  |  | 20 | 20 | 20 | 20 | 20 | 20 |  |
| Lanolin | 10 | 10 | 10 | 10 | 10 | 10 | 10 | 10 | 10 | 10 | 10 | 10 | 10 |
| Glyceryl tri-2-ethylhexanoate | 49 | 49 | 49 | 49 | 49 | 49 | 49 | 49 | 49 | 49 | 49 | 49 | 69 |
| Iron oxide red | 4 | 4 | 4 | 4 | 4 | 4 | 4 | 4 | 4 | 4 | 4 | 4 | 4 |
| Red 202 | 2 | 2 | 2 | 2 | 2 | 2 | 2 | 2 | 2 | 2 | 2 | 2 | 2 |
| Coloring | △ | ○ | ◎ | ◎ | ◎ | △ | △ | ○ | ◎ | ◎ | ◎ | △ | △ |
| Spreadability | ○ | △*1 | ○ | ○ | ○ | × | ○ | △*1 | ○ | ○ | ○ | × | ○ |
| Gloss | △ | ◎ | ◎ | ○ | ○ | △ | △ | ◎ | ◎ | ○ | ○ | △ | △ |
| Long-lastingness | ○ | × | ○ | ○ | ◎ | ◎ | ○ | × | ◎ | ○ | ◎ | ◎ | ○ |
| Shape-retaining ability | ○ | △ | ○ | ○ | ○ | △ | ○ | △ | ○ | ○ | ○ | × | ○ |

In Table 1, evaluation of "spreadability" in Comparative example 2 and Comparative example 5 (△*1) indicate that excessive softness resulted in poor spreadability.

Examples 7–13 and Comparative Examples 8–14: Stick-Shaped Lipstick Compositions

Lipstick compositions with composition blend ratios as shown in the following Table 2 were prepared, and color development, spreadability, gloss, and long-lastingness were evaluated for Examples and Comparative examples according to the aforementioned evaluation criteria. The results are shown in Table 2.

TABLE 2

|  | Comparative example | Example | | Comparative example | Example | | Comparative example | | | | | Example | | |
|---|---|---|---|---|---|---|---|---|---|---|---|---|---|---|
|  | 8 | 7 | 8 | 9 | 9 | 10 | 10 | 11 | 12 | 13 | 14 | 11 | 12 | 13 |
| Polyethylene wax (average molecular weight 500) | 1 | 15 | 25 | 30 | 15 | 15 | 15 | 15 | 15 | 15 | 15 | 9 | 12 | 14 |
| Ceresin | 14 |  |  |  |  |  |  |  |  |  |  |  |  |  |
| Microcrystalline wax |  |  |  |  |  |  |  |  |  |  |  | 6 | 4 | 2 |
| Glyceryl diisostearate | 30 | 30 | 30 | 30 | 0.1 | 50 | 60 |  |  |  |  | 30 | 30 | 30 |
| Olive oil |  |  |  |  |  |  |  | 30 |  |  |  |  |  |  |
| Liquid petrolatum |  |  |  |  |  |  |  |  | 30 |  |  |  |  |  |
| Lanolin |  |  |  |  |  |  |  |  |  | 30 |  |  |  |  |
| Glyceryl tri-2-ethylhexanoate | 49 | 49 | 39 | 34 | 78.9 | 29 | 19 | 49 | 49 | 49 | 79 | 49 | 49 | 49 |
| Red iron oxide | 4 | 4 | 4 | 4 | 4 | 4 | 4 | 4 | 4 | 4 | 4 | 4 | 4 | 4 |
| Red 202 | 2 | 2 | 2 | 2 | 2 | 2 | 2 | 2 | 2 | 2 | 2 | 2 | 2 | 2 |
| Coloring | △ | ◎ | ◎ | ◎ | ○ | ◎ | ○ | △ | × | △ | △ | ◎ | ◎ | ◎ |
| Spreadability | ○ | ○ | ○ | × | ○ | ○ | △ | ○ | ○ | △ | ◎ | ◎ | ◎ | ◎ |
| Gloss | ○ | ◎ | △ | × | ◎ | ◎ | ◎ | ○ | ○ | ○ | △ | ◎ | ◎ | ◎ |
| Long-lastingness | ○ | ○ | ◎ | ◎ | ○ | ○ | ○ | ○ | ○ | ○ | △ | ◎ | ◎ | ◎ |
| Shape-retaining ability | ◎ | ○ | ○ | × | ○ | ○ | ○ | ○ | ○ | ○ | ○ | ◎ | ◎ | ◎ |

(Preparation Method)

For Examples and Comparative examples shown in Table 1 and Table 2, the ingredients were dissolved at 90–100° C. and dispersed with a disper. Following deaeration, the mixture was poured into a lipstick container and cooled to obtain a stick-shaped lipstick composition.

(Evaluation)

As clearly indicated in Table 1 and Table 2, compositions which contained only ingredient (b) and did not contain ingredient (a) did not show improved usability. Compositions which only contained ingredient (a) did not show improved usability either. The effect of the present invention was obtained when polyethylene wax with a molecular weight of 300–700 was used.

When both ingredient (a) and ingredient (b) were combined, a synergistic improvement in the color development was observed without sacrificing spreadability, gloss, and long-lastingness when the blend ratio of ingredient (a) was 3–25 mass % and the blend ratio of ingredient (b) was 0.1–50 mass %. When ingredient (a) exceeded 25 mass % spreadability became heavy, and gloss and long-lastingness tended to become inferior, too. When olive oil, liquid petrolatum, lanolin, or glyceryl tri-2-ethylhexanoate was used instead of ingredient (b) for the liquid oil, the effect of the present invention was not observed.

Compositions of Examples had an adequate shape-retaining ability even if they did not use ceresin.

Example 14 Stick-Shaped Lipstick

| (Ingredients) | (wt %) |
|---|---|
| Microcrystalline wax | 3 |
| Polyethylene wax (average molecular weight 500) | 15.0 |
| Glyceryl trioctanoate | 22 |
| Heavy liquid petrolatum | 10 |
| Cholesteryl macadamia nut oil fatty acid | 10 |
| Glyceryl tri (hydrogenated rosin/isostearate) | 10 |
| Glyceryl diisostearate | 10 |
| Isostearyl oxystearate | 10 |
| Pigment | 10 |
| Antioxidant | Appropriate amount |
| Ultraviolet absorbent | Appropriate amount |
| Perfume | Appropriate amount |

(Preparation Method)

Lipsticks were prepared with a conventional method. They are superior in color development, spreadability, gloss, and long-lastingness, and have enough shape-retaining ability.

Example 15 Paste-Like Lipstick Composition

| (Ingredients) | (mass %) |
|---|---|
| (1) Petrolatum | 8 |
| (2) Polyethylene wax (average molecular weight 500) | 2 |
| (3) Squalane | 10 |
| (4) Castor oil | 3 |
| (5) Diglyceryl triisostearate | 5 |
| (6) Glyceryl triisostearate | 2 |
| (7) Silicone resin (molecular weight is about 5000. $(CH_3)_3SiO_{1/2}:SiO_2$ unit = 0.8:1, with a mean formula of $(CH_3)_{1.33}SiO_{1.34}$) | 25 |
| (8) Decamethyl cyclopenta siloxane | 39.5 |
| (9) Silica | 2.5 |
| (10) Pigment | 3 |
| (11) Perfume | Appropriate amount |

(Preparation Method)

Ingredients (1)–(11) were dissolved at 90–100° C. and dispersed with a disperser.

Following deaeration, the mixture was poured into a lipstick container and cooled to obtain a paste-like lipstick composition.

Example 16 Stick-Shaped Lipstick Composition

| (Ingredients) | (mass %) |
|---|---|
| (1) Polyethylene wax (average molecular weight 500) | 8 |
| (2) Candelilla wax | 3 |
| (3) Squalane | 8 |
| (4) Diglyceryl triisostearate | 10 |
| (5) Macadamia nut oil fatty acid ester | 2.5 |
| (6) Glyceryl tri-2-ethylhexanoate | 4.5 |
| (7) Silicone resin (molecular weight is about 6000. $(CH_3)_3SiO_{1/2}:SiO_2$ unit = 0.8:1, with a mean formula of $(CH_3)_{1.33}SiO_{1.34}$) | 20 |
| (8) Decamethyl cyclopenta siloxane | 34 |
| (9) Fine particle barium sulfate | 5 |
| (10) Pigment | 5 |
| (11) Perfume | Appropriate amount |

(Preparation Method)

Ingredients (1)–(11) were dissolved at 90–100° C. and dispersed with a disper. Following deaeration, the mixture was poured into a lipstick container and cooled to obtain a stick-shaped lipstick composition.

Example 17 Emulsified Stick-Shaped Lipstick Composition

| (Ingredients) | (mass %) |
|---|---|
| (1) Paraffin wax | 5 |
| (2) Microcrystalline wax | 4 |
| (3) Polyethylene wax (average molecular weight 500) | 5 |
| (4) Diglyceryl triisostearate | 3 |
| (5) Glyceryl diisostearate | 4 |
| (6) Macadamia nut oil | 3 |
| (7) Polybutene | 3 |
| (8) Diisostearyl malate | 4 |
| (9) Silicone resin (molecular weight is about 8000. $(CH_3)_3SiO_{1/2}:SiO_2$ unit = 0.8:1, with a mean formula of $(CH_3)_{1.33}SiO_{1.34}$) | 30 |
| (10) Decamethylcyclopentasiloxane | 10.5 |
| (11) Octamethylcyclotetrasiloxane | 7 |
| (12) Dimethylpolysiloxane (viscosity 6 cs) | 5 |
| (13) Silica | 3 |
| (14) Synthesized sodium magnesium silicate | 1 |
| (15) Polyoxyethylene/methyl poly siloxane copolymer | 2 |
| (16) Ion-exchange water | 5 |
| (17) Glycerin | 1 |
| (18) Pigment | 4.5 |
| (19) Perfume | Appropriate amount |

(Preparation Method)

Ingredients (1)–(15), (18) and (19) were dissolved at 90–100° C. and dispersed with a disperser. (16) and (17)

were added to this and dispersed further; and, after deaeration, the mixture was poured into a lipstick container and cooled to obtain an emulsified stick-shaped lipstick composition.

Example 18 Stick-Shaped Lipstick Composition

| (Ingredients) | (mass %) |
|---|---|
| (1) Polyethylene wax (average molecular weight 500) | 8 |
| (2) Candelilla wax | 3 |
| (3) Squalane | 8 |
| (4) Diglyceryl triisostearate | 3 |
| (5) Macademia nut oil fatty acid ester | 2.5 |
| (6) Glyceryl tri-2-ethylhexanoate | 1.5 |
| (7) Silicone resin (molecular weight is about 6000. $(CH_3)_3SiO_{1/2}:SiO_2$ unit = 0.8:1, with a mean formula of $(CH_3)_{1.33}SiO_{1.34}$) | 20 |
| (8) Decamethyl cyclopenta siloxane | 43.95 |
| (9) Fine particle barium sulfate | 5 |
| (10) Pigment | 5 |
| (11) Camphor | 0.05 |
| (12) Perfume | Appropriate amount |

(Preparation Method)

Ingredients (1)–(12) were dissolved at 90–100° C. and dispersed with a disperser. Following deaeration, the mixture was poured into a lipstick container and cooled to obtain a stick-shaped lipstick composition.

Example 19 Emulsified Stick-Shaped Lipstick Composition

| (Ingredients) | (mass %) |
|---|---|
| (1) Polyethylene wax (average molecular weight 500) | 10 |
| (2) Microcrystalline wax | 4 |
| (3) Glyceryl diisostearate | 7 |
| (4) Diglyceryl triisostearate | 3 |
| (5) Macademia nut oil | 3 |
| (6) Polybutene | 3 |
| (7) Diisostearyl malate | 1 |
| (8) Silicone resin (molecular weight is about 8000. $(CH_3)_3SiO_{1/2}:SiO_2$ unit = 0.8:1, with a mean formula of $(CH_3)_{1.33}SiO_{1.34}$) | 30 |
| (9) Decamethylcyclopentasiloxane | 10.46 |
| (10) Octamethylcyclotetrasiloxane | 7 |
| (11) Dimethylpolysiloxane (viscosity 6 cs) | 5 |
| (12) Silica | 3 |
| (13) Synthesized sodium magnesium silicate | 1 |
| (14) Polyoxyethylene/methyl poly siloxane copolymer | 2 |
| (15) Ion-exchange water | 5 |
| (16) Glycerin | 1 |
| (17) Pigment | 4.5 |
| (18) Pantothenyl ethyl ether | 0.01 |
| (19) Pyridoxine hydrochloride | 0.02 |
| (20) Royal jelly extract | 0.01 |
| (21) Perfume | Appropriate amount |

(Preparation Method)

Ingredients (1)–(14) and (17)–(21) were dissolved at 90–100° C. and dispersed with a disperser. (15) and (16) were added to this and dispersed further; and, after deaeration, the mixture was poured into a lipstick container and cooled to obtain an emulsified stick-shaped lipstick composition.

Example 20 Stick-Shaped Lipstick Composition

| | (Ingredients) | (mass %) |
|---|---|---|
| A. | Lipstick base | |
| | (1) Carnauba wax | 0.5 |
| | (2) Candelilla wax | 5 |
| | (3) Polyethylene wax (average molecular weight 500) | 10 |
| | (4) Squalane | 30 |
| | (5) Glyceryl triisostearate | 10 |
| | (6) Glyceryl diisostearate | 37.5 |
| B. | Water-containing composition | |
| | (7) Hydroxy-propylated β-cyclodextrin | 1 |
| | (8) Cholesterol ester (isostearic acid) | 3.5 |
| | (9) Glycerin | 0.5 |
| | (10) Purified water | 2 |
| C. | Other bases | |
| | (11) Coloring material | Appropriate amount |
| | (12) Perfume | Appropriate amount |
| | (13) Preservatives | Appropriate amount |

(Preparation Method)

(7), melted in (10) (0.5 mass %), was added to (8) which was kept at 60° C., and stirring was conducted for 10 minutes with a disper. The rest of (10) (1.5 mass %) and (9) were added to this, followed by a 10-minute stirring, to obtain water-containing composition (B).

Lipstick base (A) was melted at 80° C., to which water-containing composition (B) was added, and, after a 10-minute stirring with a disper, (11)–(13) were added; after dispersing and stirring, the mixture was molded to obtain a stick-shaped lipstick composition.

Example 21 Stick-Shaped Lipstick Composition

| (Ingredients) | (mass %) |
|---|---|
| (1) Polyethylene wax (average molecular weight 500) | 4 |
| (2) Candelilla wax | 8 |
| (3) Glyceryl diisostearate | 2 |
| (4) Organic silicone resin (Molecular weight is about 20,000. $(CH_3)_3SiO_{1/2}$ unit:$SiO_2$ unit = 0.5:1, with a mean formula of $(CH_3)_{1.8}SiO_{1.1}$) | 10 |
| (5) Decamethyl cyclopenta siloxane | 54.95 |
| (6) Perfluoroalkyl modified methyphenyl polysiloxane | 3 |
| (7) Methylphenylpolysiloxane (15 CS/25° C.) | 2 |
| (8) POE (25) POP (20) tetradecyl ether | 1 |
| (9) Ion-exchange water | 5 |
| (10) Glycerin | 2 |
| (11) Propylene glycol | 1 |
| (12) Titanium dioxide | 4.5 |
| (13) Red 201 | 0.5 |
| (14) Red 202 | 2 |
| (15) Red 223 | 0.05 |
| (16) Ultraviolet absorbent | Appropriate amount |
| (17) Antioxidant | Appropriate amount |
| (18) Perfume | Appropriate amount |

(Preparation Method)

(13)–(15) were thoroughly stirred and mixed, and then added to (1)–(8) and (16)–(18) which had been heated and dissolved, and the mixture was thoroughly mixed (oil phase). Separately, (9)–(11) were heated and dissolved (water phase). The water phase was added to the oil phase; after emulsification using a homogenizer, the mixture was poured into a mold and quickly cooled to obtain a stick-shaped lipstick composition.

Example 22 Stick-Shaped Emulsified Lip Cream

| (Ingredients) | | (mass %) |
|---|---|---|
| A. Emulsified base | | |
| (1) | Synthesized hectorite | 3 |
| (2) | Polyoxyethylene methyl poly siloxane copolymer | 0.5 |
| (3) | Methylphenyl poly siloxane | 10 |
| (4) | Purified water | 1.5 |
| (5) | Glycerin | 0.2 |
| (6) | L-arginine hydrochloride | 0.5 |
| B. Oil phase | | |
| (7) | Microcrystalline wax | 1 |
| (8) | Polyethylene wax (average molecular weight 500) | 14 |
| (9) | Glyceryl tri-2-ethylhexanoate | 40 |
| (10) | Diisostearyl malate | 19.3 |
| (11) | Glyceryl diisostearate | 10 |

(Preparation Method)

First, an emulsified base was prepared with (1)–(6). That is, (1) and (2) were dispersed in (3) at ordinary temperatures (oil phase). (4)–(6) were mixed and dissolved (water phase), which was then added to and dispersed in said oil phase to obtain the emulsified base. Said emulsified base was then added to the oil phase which had been prepared by heating and dissolving (7)–(11), followed by thorough stirring and mixing; and the mixture was poured into a metal mold and allowed to cool to obtain a stick-shaped emulsified lip cream.

INDUSTRIAL APPLICABILITY

The present invention provides a lipstick composition which is superior in terms of usability (spreadability, gloss, and long-lastingness) and drastically improves the color development.

Also, a lipstick composition with a superior shape-retaining ability is provided without using ceresin for the shape-retaining agent.

What is claimed is:

1. A lipstick composition comprising:
   (a) polyethylene wax having an average molecular weight of 300–700,
   (b) microcrystalline wax; and
   (c) 0.1–50 mass % of one, two or more liquid oils having one —OH group in the structure,
   wherein polyethylene wax and microcrystalline wax are blended in a mass ratio of 6:4–9:1, polyethylene wax and the microcrystalline wax are blended so as to comprise 3–25 mass % of the composition, and the composition contains substantially no ceresin.

2. A lipstick composition as defined in claim 1 wherein ingredient (b) is one or more chosen from a group consisting of glyceryl diisostearate, diglyceryl triisostearate, and isostearyl oxystearate.

3. A method for retaining the shape of a substantially ceresin-free lipstick composition comprising blending therein:
   (a) 3–25 mass % of a blend of polyethylene wax having an average molecular weight 300–700 and microcrystalline wax; and
   (b) 0.1–50 mass % of one, two or more liquid oils having one —OH group in the structure,
   wherein polyethylene wax and microcrystalline wax are blended in a mass ratio of 6:4–9:1.

4. The method of claim 3, wherein (b) is one or more selected from the group consisting of glyceryl diisostearate, diglyceryl triisostearate, and isostearyl oxystearate.

* * * * *